US008790271B2

(12) United States Patent
Jang

(10) Patent No.: US 8,790,271 B2
(45) Date of Patent: Jul. 29, 2014

(54) PORTABLE DEVICE FOR CALCULATING CONSUMED CALORIES

(75) Inventor: Yong Won Jang, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 223 days.

(21) Appl. No.: 12/958,124

(22) Filed: Dec. 1, 2010

(65) Prior Publication Data

US 2011/0152636 A1 Jun. 23, 2011

(30) Foreign Application Priority Data

Dec. 18, 2009 (KR) .................. 10-2009-0127489
Aug. 2, 2010 (KR) .................. 10-2010-0074704

(51) Int. Cl.
*A61B 5/08* (2006.01)

(52) U.S. Cl.
USPC .............................. 600/531; 600/538

(58) Field of Classification Search
USPC ............................ 600/531, 532, 534, 538
See application file for complete search history.

(56) References Cited

U.S. PATENT DOCUMENTS

| 5,732,709 | A | | 3/1998 | Tacklind et al. | |
|---|---|---|---|---|---|
| 6,126,613 | A | * | 10/2000 | Edwards et al. | 600/539 |
| 6,478,736 | B1 | * | 11/2002 | Mault | 600/300 |
| 6,571,200 | B1 | * | 5/2003 | Mault | 702/182 |
| 2003/0065275 | A1 | * | 4/2003 | Mault et al. | 600/531 |
| 2003/0226695 | A1 | * | 12/2003 | Mault | 177/25.16 |
| 2007/0051369 | A1 | | 3/2007 | Choi et al. | |
| 2008/0228098 | A1 | * | 9/2008 | Popov et al. | 600/537 |
| 2008/0285805 | A1 | * | 11/2008 | Luinge et al. | 382/107 |
| 2008/0319334 | A1 | * | 12/2008 | Yamamori | 600/532 |
| 2009/0195350 | A1 | * | 8/2009 | Tsern et al. | 340/3.1 |
| 2010/0234714 | A1 | * | 9/2010 | Mercier et al. | 600/388 |

FOREIGN PATENT DOCUMENTS

| EP | 1681018 A1 | 7/2006 |
|---|---|---|
| JP | 2002-200059 A | 7/2002 |
| JP | 2004-097589 A | 4/2004 |
| KR | 10-0697646 A | 3/2007 |
| KR | 2009-0039124 A | 4/2009 |
| WO | WO-2005/034750 A1 | 4/2005 |

* cited by examiner

*Primary Examiner* — Navin Natnithithadha
*Assistant Examiner* — Etsub Berhanu
(74) *Attorney, Agent, or Firm* — Rabin & Berdo, P.C.

(57) ABSTRACT

A portable device for measuring a consumed calories includes: a respiration measurement device measuring an amount of air inhaled into a user's nose to acquire and output a respiration signal; a plurality of movement detection devices acquiring and outputting acceleration signals reflecting (or indicating) the magnitude and direction of a movement of each part of the user's body; and a controller recognizing the amount of a user's movements and movement patterns by analyzing the acceleration signal, recognizing an intensity of an exercise by analyzing the respiration signal, and calculating a consumed calories in consideration of the amount of the user's movements, the movement patterns, and the intensity of exercise. A user's consumed calories can be precisely calculated by recognizing the user's movement and even the user's respiration rate.

17 Claims, 8 Drawing Sheets

① NUMBER OF BREATHS = THE NUMBER OF GENERATED INHALATIONS AND EXHALATIONS = 3
② RESPIRATION RATE = 3+4+3 = 10

PORTABLE DEVICE FOR CALCULATING CONSUMED CALORIES

CROSS-REFERENCE TO RELATED APPLICATIONS

This application claims the priority of Korean Patent Application Nos. 10-2010-0074704 filed on Aug. 2, 2010 and 10-2009-0127489 filed on Dec. 18, 2009 in the Korean Intellectual Property Office, the disclosure of which are incorporated herein by reference.

BACKGROUND OF THE INVENTION

1. Field of the Invention

The present invention relates to a device for calculating a user's consumed calories and, more particularly, to a portable device for precisely calculating a user's consumed calories by accurately recognizing a user's movements and even the amount of the user's respiration.

2. Description of the Related Art

As the so-called ubiquitous technique has been introduced into daily life, people can do their job as required any time and any place, and in line with this, techniques for the measurement and management of personal health have been advanced in the field of ubiquitous healthcare.

However, in spite of the development of ubiquitous healthcare in various fields, accurately measuring a person's consumed calories is not easy and still remains at issue.

There have been many attempts to calculate a user's consumed calories by measuring the user's movement by using an acceleration sensor, but this method has a limitation in further improvements to the accuracy thereof, and, in particular, only the use of the acceleration sensor makes the limitation clearer.

SUMMARY OF THE INVENTION

An aspect of the present invention provides a portable device for measuring a user's consumed calories capable of recognizing a user's movement three-dimensionally to thus improve accuracy of measurement.

Another aspect of the present invention provides a portable device for calculating a user's consumed calories by using a respiration measurement sensor for measuring a user's respiration rate and an acceleration sensor together, to thus increase the accuracy of measurement.

According to an aspect of the present invention, there is provided a portable device for measuring consumed calories, including: a respiration measurement device measuring an amount of air inhaled into a user's nose to acquire and output a respiration signal; a plurality of movement detection devices acquiring and outputting acceleration signals reflecting (or indicating) the magnitude and direction of a movement of each part of the user's body; and a controller recognizing the amount of a user's movements and movement patterns by analyzing the acceleration signal, recognizing the intensity of an exercise by analyzing the respiration signal, and calculating consumed calories in consideration of the amount of a user's movements, the movement patterns, and the intensity of exercise.

The portable device may further include: one or more temperature sensors measuring one or more of the user's mouth temperature (i.e., the temperature within the user's oral cavity), the user's skin temperature, and an external body temperature.

The controller may calculate consumed calories further in consideration of one or more of the user's mouth temperature, the user's skin temperature, and the external body temperature, in addition to the amount of movements, the movement patterns, and the respiration rate.

The respiration measurement device may include: a respiration measurement sensor measuring the amount of air inhaled into the user's nose; and a signal processing unit calculating the respiration rate from the amount of air which has been measured by the respiration measurement sensor, converting the respiration rate into a signal recognizable to the controller, and outputting the converted signal.

The respiration measurement sensor may include: a glass frame having a nose cover formed to cover the user's nose; and a signal generation unit placed on the nose cover and generating a signal corresponding to the amount of air inhaled into the user's nose or exhaled from the user's nose.

The signal generation unit may include: a body having an inhalation passage; a turbine installed in the inhalation passage so as to rotate according to inhalation through the inhalation passage; and a plurality of coils installed at an inner side of the inhalation passage in order to generate an AC signal according to alternate magnetic fields resulting from the rotation of the turbine.

The body may include: the inhalation passage; an exhalation passage accommodating the inhalation passage therein; a suction valve plate installed in the inhalation passage and opened only for inhalation; a discharge valve plate installed in the exhalation passage and opened only for exhalation; and a frame fixing the inhalation passage in the interior of the exhalation passage and supporting the position of the turbine.

The respiration measurement sensor may further include a mouth piece implemented to be separated from the glass frame or placed on the glass frame such that it is positioned at a lower side of the nose cover.

The mouth piece may include a temperature sensor for measuring the user's mouth temperature.

The signal processing unit may include: a filter unit converting an input signal into a voltage signal, filtering the converted voltage signal, and amplifying the filtered voltage signal; an analog-to-digital conversion unit converting an output from the filter unit into a digital signal; a calculation unit analyzing a generation pattern of the digital signal to calculate the amount of respiration; and an external interface providing an interface with the controller.

The signal processing unit may include: a memory storing an output from the calculation unit; and a power source unit providing a power source required for driving the signal processing unit and charging the power source by using an AC signal provided from the respiration measurement sensor.

Each of the plurality of movement detection devices may include: a 3-axis acceleration sensor acquiring the magnitude and direction of a movement of each body part; and a signal processing unit outputting the magnitude and direction of a movement acquired by the 3-axis acceleration sensor in the form of a signal recognizable to the controller.

The signal processing unit may include: a filter unit converting an input signal into a voltage signal, filtering the converted voltage signal, and amplifying the filtered voltage signal; an analog-to-digital conversion unit converting an output from the filter unit into a digital signal; a calculation unit analyzing a generation pattern of the digital signal to calculate the amount of respiration; and an external interface providing an interface with the controller; and a memory storing an output from the calculation unit.

Each of the plurality of movement detection devices may include one or more of a temperature sensor for measuring a skin temperature and an external body temperature.

When the controller calculates consumed calories, it may calculate adjustable consumed calories in consideration of signals acquired by the respiration measurement device and the plurality of movement detection devices.

The respiration measurement device and the plurality of movement detection devices may be coupled to a docking station.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

Figure 1:
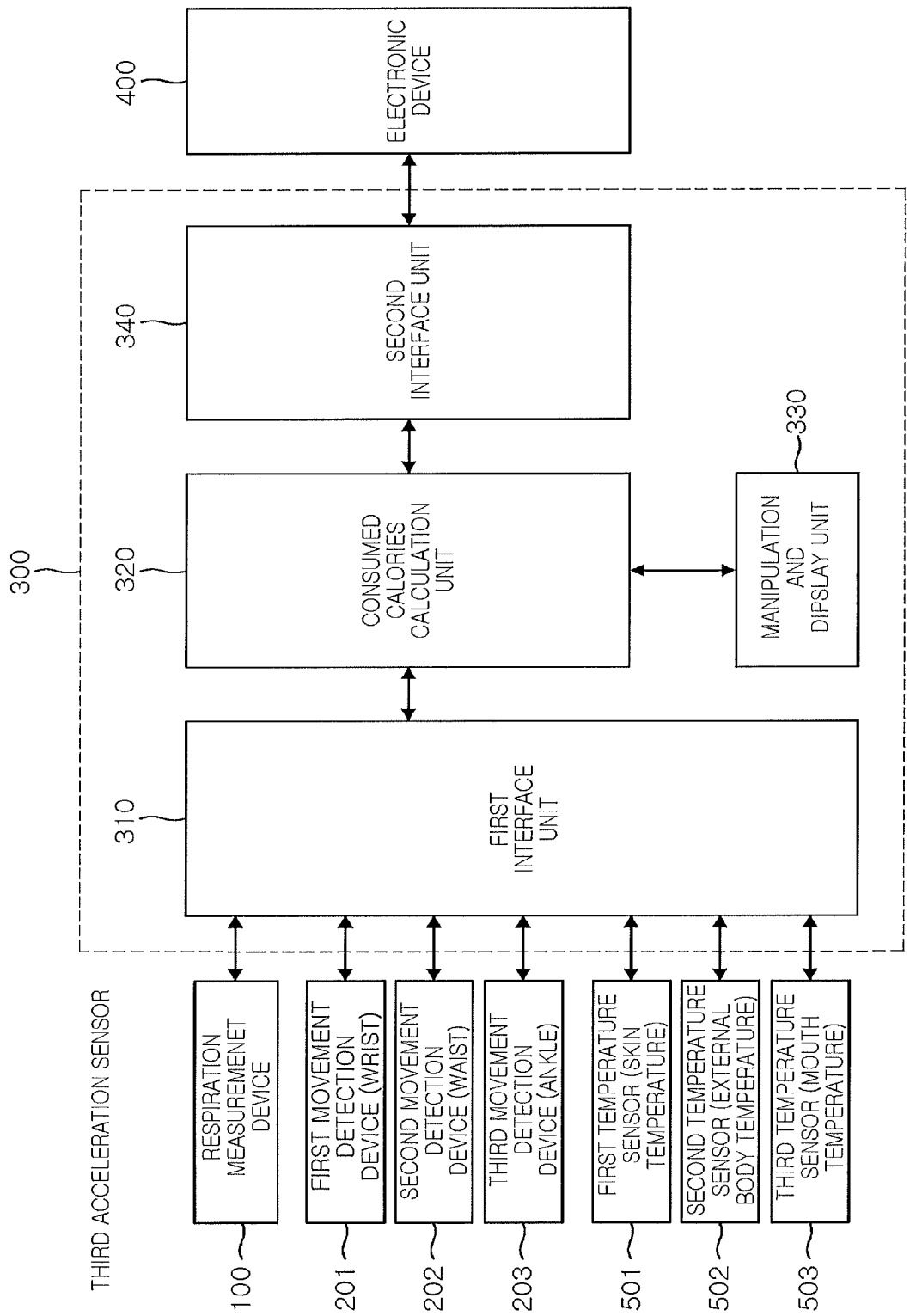
FIG. 1 is a schematic block diagram of a portable device for measuring consumed calories according to an exemplary embodiment of the present invention.

The present invention may be modified variably and may have various embodiments, particular examples of which will be illustrated in drawings and described in detail.

However, it should be understood that the following exemplifying description of the invention is not intended to restrict the invention to specific forms of the present invention but rather the present invention is meant to cover all modifications, similarities and alternatives which are included in the spirit and scope of the present invention.

While terms such as "first" and "second," etc., may be used to describe various components, such components must not be understood as being limited to the above terms. The above terms are used only to distinguish one component from another. For example, a first component may be referred to as a second component without departing from the scope of rights of the present invention, and likewise a second component may be referred to as a first component. The term "and/or" encompasses both combinations of the plurality of related items disclosed and any item from among the plurality of related items disclosed.

When a component is mentioned as being "connected" to or "accessing" another component, this may mean that it is directly connected to or accessing the other component, but it is to be understood that another component may exist therebetween. On the other hand, when a component is mentioned as being "directly connected" to or "directly accessing" another component, it is to be understood that there are no other components in-between.

The terms used in the present application are merely used to describe particular embodiments, and are not intended to limit the present invention. An expression used in the singular encompasses the expression of the plural, unless it has a clearly different meaning in context. In the present application, it is to be understood that the terms such as "including" or "having," etc., are intended to indicate the existence of the features, numbers, operations, actions, components, parts, or combinations thereof disclosed in the specification, and are not intended to preclude the possibility that one or more other features, numbers, operations, actions, components, parts, or combinations thereof may exist or may be added.

Unless otherwise defined, all terms used herein, including technical or scientific terms, have the same meanings as those generally understood by those with an ordinary knowledge in the field of art to which the present invention pertains. Terms such as those defined in a generally used dictionary are to be interpreted as having meanings equal to the contextual meanings in the relevant field of art, and are not to be interpreted as having ideal or excessively formal meanings unless clearly defined as having such in the present application.

Embodiments of the present invention will be described below in detail with reference to the accompanying drawings, where those components are rendered using the same reference number that are the same or are in correspondence, regardless of the figure number, and redundant explanations are omitted.

FIG. 1 is a schematic block diagram of a portable device for measuring consumed calories according to an exemplary embodiment of the present invention.

With reference to FIG. 1, the portable device for measuring consumed calories may be implemented in the form of being portable by a user and include a respiration measurement device 100, a plurality of movement detection devices 201 to 203, and a controller 300. The portable device may further include a plurality of temperature sensors 501 to 503 as necessary.

The function of each element will be described in detail as follows.

The respiration measurement device 100 may be implemented to cover a user's nose or be inserted in the nostrils to measure the amount of air inhaled into the user's nose to calculate the amount of the user's respiration.

The plurality of movement detection devices 201 to 203 may generate and output a plurality of acceleration signals reflecting the magnitude and direction of the movements of the user's body parts. In this case, the plurality of movement detection devices 201 to 203 are worn on (or attached to) a user's body parts representing the user's three-dimensional movements, namely, the user's body parts where signal values of the plurality of movement detection devices 201 to 203 are largest and frequently change according to the user's movement. Whenever the user moves, each of the plurality of movement detection devices 201 to 203 generates and outputs an acceleration signal having a signal value corresponding to the magnitude and direction of the movements of the user's body parts from the positions where the plurality of movement detection devices 201 to 203 are attached.

Figure 2:
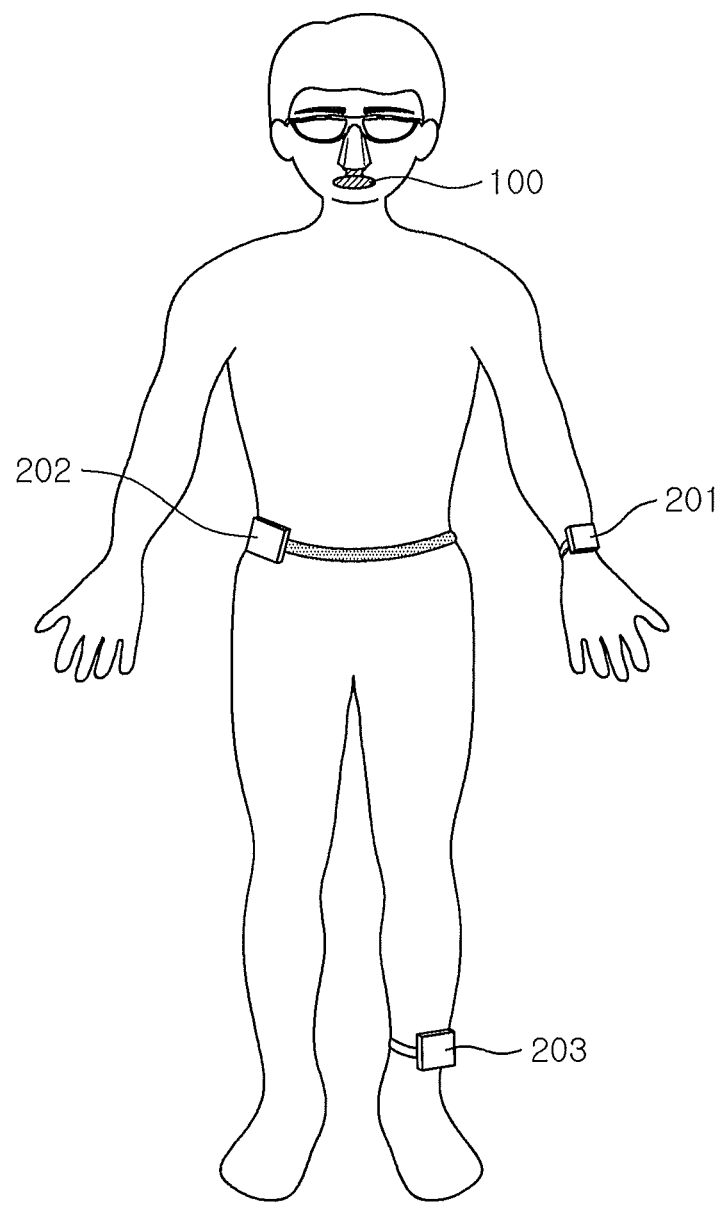
FIG. 2 illustrates a person who wearing a respiration measurement device and a plurality of movement detection devices according to an exemplary embodiment of the present invention.

In an exemplary embodiment of the present invention, as shown in FIG. 2, the user's body parts representing the user's three-dimensional movements will be defined as the user's wrist, ankle, and waist for the sake of brevity, and it is assumed that the plurality of movement detection devices 201 to 203 are attached to these body parts. The acceleration sensors attached to the user's wrist, waist, and ankle will be referred to as a first movement detection device 201, a second movement detection device 202, and a third movement detection device 203, respectively.

The movement detection devices 201 to 203 may be variably implemented as a clock type device, a belt type device, and a passometer type device, respectively, in consideration of the user's request or preference or the parts of the user's body where the movement detection devices 201 to 203 are worn.

These movement detection devices 201 to 203 measure one or more of the user's skin temperature, the user's mouth temperature, and an external body temperature, and generate and output a temperature signal.

The temperature sensors 501 to 503 may be put on various body parts. For example, the temperature sensors 501 to 503 may be positioned on at least one or more of the user's wrist, waist and ankle to measure the user's skin temperature and external body temperature. Also, the temperature sensors 501 to 503 may be positioned within the user's mouth to measure the user's mouth temperature. Also, each of the temperature sensors 501 to 503 may be implemented as an independent device or may be installed within the movement detection devices 201 to 203 or the respiration measurement device 100.

In the present exemplary embodiment, for the sake of brevity, as shown in FIG. 2, the temperature sensor installed in the first movement detection device 201 to measure the temperatures of the skin of the users wrist and an external body temperature will be referred to as the first and second temperature sensors 501 and 502, and the temperature sensor installed in the respiration measurement device 100 to measure the user's mouth temperature will be referred to as the third temperature sensor 503.

The controller 300 analyzes acceleration signals provided from the plurality of movement detection devices 201 to 203 to recognize the amount of a user's movements and movement patterns, and analyzes the respiration rate from the respiration measurement device 100 to recognize the intensity of an exercise. Then, the controller 300 calculates the user's consumed calories in consideration of the amount of the user's movements, movement patterns, and movement intensity as recognized. Also, besides the user's amount of movements, movement patterns, and the intensity of exercise, if necessary, the controller 300 may calculate the user's consumed calories in consideration of the user's skin temperature, respiration temperature, external body temperature, and the like.

To this end, the controller 300 may include a first interface unit 310 performing interfacing with the respiration measurement device 100, the plurality of movement detection devices 201 to 203, and one or more temperature sensors 501 to 503, a consumed calories calculation unit 320 analyzing signals acquired by the plurality of movement detection devices 201 to 203 and the respiration measurement device 100 to recognize the amount of the user's movements, movement patterns, and the intensity of an exercise and calculating the user's consumed calories in consideration of the amount of the user's movements, movement patterns, and the intensity of exercise, the user's skin temperature and mouth temperature, external body temperature, and the like, altogether, and a manipulation and display unit 330 displaying the operation results from the controller 300 (in particular, the calculation results from the consumed calories calculation unit 320) or acquiring various pieces of information (e.g., information about a user's body, the type of activity engaged in, and the like) for controlling the controller 300 Also, the controller 300 may display a movement pattern, which has been recognized by the consumed calories calculation unit 320, through the manipulation and display unit 330, and in this case, when the user acknowledges whether or not the movement pattern recognized by the consumed calories calculation unit 320 is proper, the controller 300 may calculate the consumed calories accordingly.

The consumed calories calculation unit 320 may acquire three types of acceleration signals having signal values corresponding to the magnitude and direction of the movements of the user's arm, leg, and trunk (torso) through the plurality of movement detection devices 201 to 203, analyze them to calculate the body parts that make a movement over time and the amount of movements of the corresponding body parts, and keep tracking them to recognize the amount of a user's movements and movement patterns. In addition, the consumed calories calculation unit 320 finally calculates the consumed calories in consideration of the user's amount of movements, movement patterns, and the intensity of exercise altogether, and in this case, the weight of considering the amount of the user's movements, movement pattern, and the intensity of exercise may be changed in consideration of the types of the movement patterns, an external body temperature, and the like.

In order to increase the accuracy of calculation, the consumed calories calculation unit 320 may calculate the consumed calories in consideration of the user's skin temperature and mouth temperature, the external body temperature, and the like, measured by the one or more temperature sensors 501 to 503, in addition to the amount of the user's movements, movement patterns, and the intensity of exercise. Namely, the consumed calories calculation unit 320 may measure a change in the user's body temperature when the user moves by using the difference between the user's mouth temperature and the temperature of the user's body surface, or additionally estimating consumed calories in a case in which the user moves in a cold place or in a hot place in consideration of the external body temperature.

The controller 300 may further include a second interface 340 for interfacing with an electronic device 400 such as a personal computer (PC), a mobile phone, a notebook computer, or the like. The electronic device 400 may be provided with information generated by the portable device for calculating consumed calories through the second interface unit 340, and perform various operations such as generating supplementary information required for obesity management, exercise management, disease management, and the like, or transmitting the generated supplementary information to an external server, based on the provided information.

The portable device for measuring consumed calories may be able to measure a ball game such as football, basket ball, and the like, including a basic exercise such as walking, running, going up the stairs, and the like. In addition, the portable device for measuring consumed calories may be able to analyze movement patterns in daily life such as sitting and taking a break, dish-washing, and the like, and many of other movement patterns such as doing office work at a desk, and the like.

Information regarding the intensity of an exercise may be obtained from the size of an acceleration signal, the strength of a respiration signal, and the like, and also consumed calories with respect to a muscular exercise which does not make much movement but has a large amount of movements. Namely, consumed calories can be calculated while adjusting the weight of considering signals acquired by the respiration measurement device 100 and the plurality of movement detection devices according to the types of user's movements (namely, while adjusting the weight of considering the amount of the user's movements, movement patterns, the intensity of exercise, skin temperature, mouth temperature, external body temperature, and the like).

For example, when calorie consumption is made in a static state such as a muscular exercise, analysis of only the amount of a user's movements and movement patterns would increase an error, so in this case, the signal from the respiration measurement device 100 and the signals from the temperature sensors 501 to 503 may be given more weight to be analyzed to obtain consumed calories, thus reducing an error.

Figure 3:
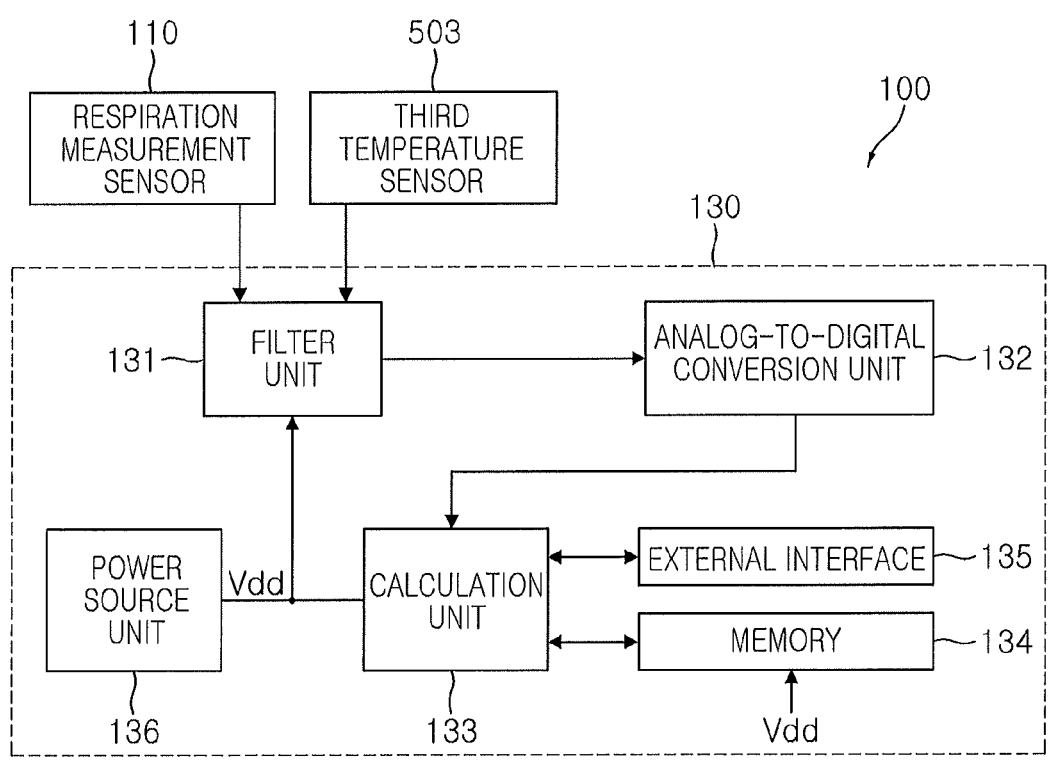
FIG. 3 is a schematic block diagram of the respiration measurement device according to an exemplary embodiment of the present invention.

FIG. 3 is a schematic block diagram of the respiration measurement device according to an exemplary embodiment of the present invention.

With reference to FIG. 3, the respiration measurement device 100 may include a respiration measurement sensor 110 and a signal processor 130. The respiration measurement device 100 may further include a third temperature sensor 503 for measuring mouth temperature as necessary.

Figure 4A:
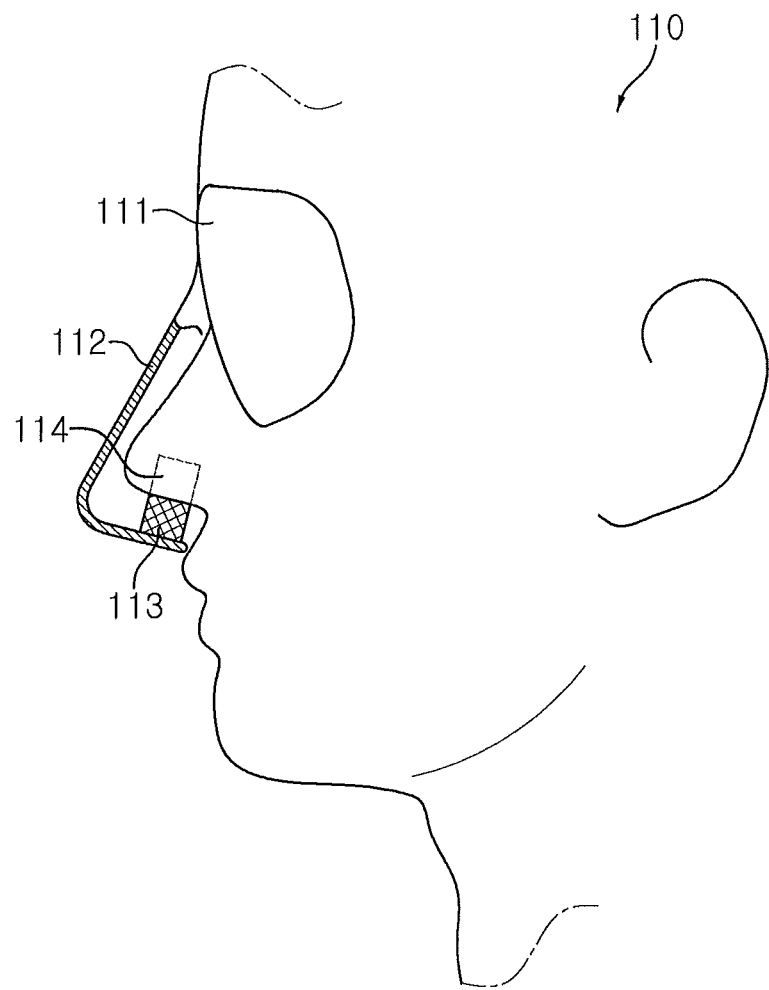
FIGS. 4a and 4b illustrate an outer appearance of the respiration measurement device according to an exemplary embodiment of the present invention.
Figure 4B:
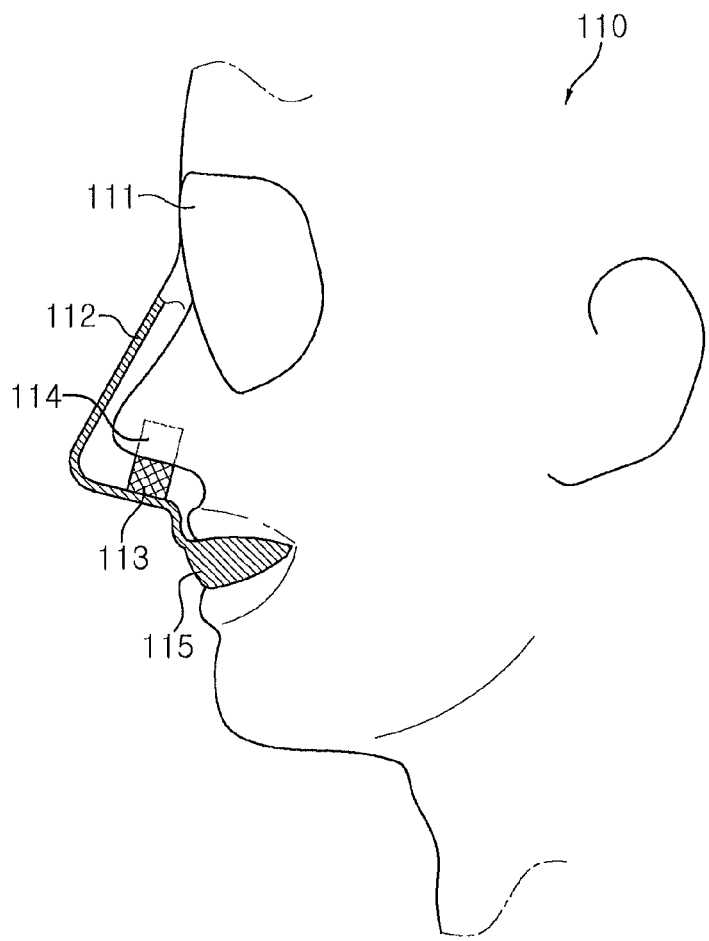

The respiration measurement sensor 110 may be implemented in the form as shown in FIGS. 4a and 4b to measure the amount of air inhaled into the user's nose and inform the signal processing unit 130 accordingly.

The signal processing unit 130 calculates the amount of the user's respiration based on the amount of air which has been measured by the respiration measurement sensor 110, converts the amount of the user's respiration and the mouth temperature into a signal recognizable to the controller 300, and provides the converted signal to the controller 300.

To this end, the signal processing unit 130 may include a filter unit 131 converting signals inputted from the respiration measurement sensor 110 and the third temperature sensor 503 into voltages and filtering and amplifying the same to improve signal characteristics, an analog-to-digital conversion unit 132 converting an output signal from the filter unit 131 into a digital signal, a calculation unit 133 analyzing a generation pattern of the output signal from the analog-to-digital conversion unit 132 to calculate the respiration rate, a memory 134 storing an output from the calculation unit 133, an external interface 135 performing interfacing with the controller 300 to provide an output from the calculation unit 133 or the information stored in the memory 134 to the controller 300, and a power source unit 136 providing power required for driving the signal processing unit 130.

The power source unit 136 charges power by using an induction current generated through the respiration measurement sensor 110 to thus lengthen a usage period of the respiration measurement device 100. Namely, the induction current generated by the respiration measurement sensor 110 can be collected to be used as power, thereby lengthening a battery driving time or charging a battery.

The calculation unit 133 may analyze a waveform of a signal inputted from the respiration measurement sensor 110 to derive a respiration interval and various types of information related to breath.

Figure 5:
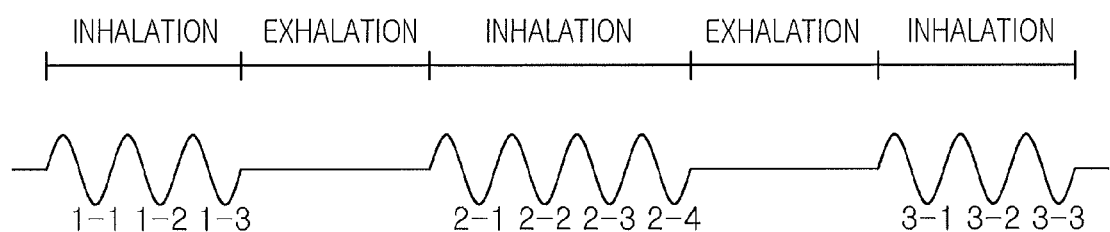
FIG. 5 is a view for explaining a method for calculating a respiration rate of the respiration measurement device according to an exemplary embodiment of the present invention.

For example, as shown in FIG. 5, the calculation unit 133 may classify an interval during which an induction current is generated as an inhalation generation interval, an interval during which the induction current is not generated as an exhalation generation interval, derive the number of breaths from the number of generated inhalations and exhalations, and derive the amount of respiration from the number of generated peaks of the exhalations.

FIGS. 4a and 4b illustrate an outer appearance of the respiration measurement device according to an exemplary embodiment of the present invention.

First, as shown in FIG. 4a, the respiration measurement sensor 110 may be implemented in the form of glasses having a nose cover formed to cover the user's nose. In detail, the respiration measurement sensor 110 may include an eyeglass frame 111 having a nose cover 112 formed to cover the user's nose, and a signal generation unit 113 mounted on the user's cover 112 to generate a signal having a value corresponding to the amount of air inhaled into or exhaled from the user's nose.

As shown in FIG. 4b, the respiration measurement sensor 110 is implemented such that a mouth piece 115 is connected to the nose cover 112, and the third temperature sensor 503 is installed in the mouth piece 115 to measure the user's body temperature.

The respiration measurement sensors 110 illustrated in FIGS. 4a and 4b are merely typical examples and may be variably modified depending on usage conditions. For example, the respiration measurement device 100 may be variably modified such that only the nose cover 112 is provided or such that the nose cover 112 and the mouth piece 115 are separated.

The structure of the respiration measurement sensor 110 will now be described in more detail with reference to FIGS. 6a and 6b.

Figure 6A:
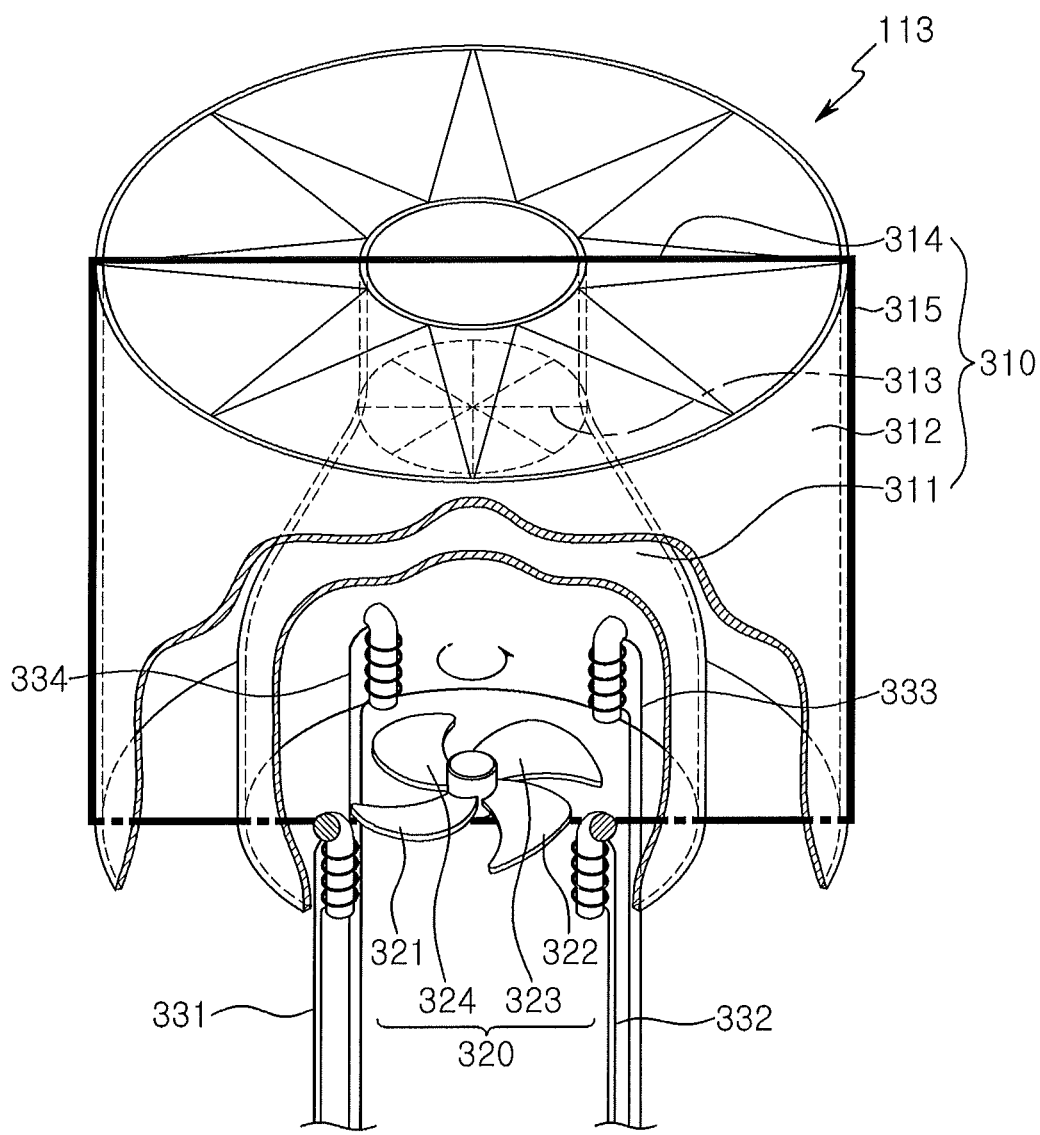
FIGS. 6a and 6b illustrate the structure of a respiration measurement sensor of the respiration measurement device according to an exemplary embodiment of the present invention.

First, as shown in FIG. 6a, the signal generation unit 113 includes a body 310 including an inhalation passage 311, an exhalation passage 312 accommodated in the interior of the inhalation passage 311, a suction valve plate 313 installed in the inhalation passage 311 and open only when an inhalation occurs, an exhaust valve plate 314 installed in the exhalation passage 312 and open only when an exhalation occurs, and a frame 315 fixing the inhalation passage 311 within the exhalation passage 312 and supporting the location of a turbine 320.

In this case, when exhalation occurs, moisture may be slightly collected in the discharge valve plate 314 due to moisture of air, so preferably, the suction valve plate 313 is positioned under the discharge valve plate 314 to allow dried air to pass through the exhaust valve plate 314.

The signal generation unit 113 may further include a turbine 320 installed in the exhalation passage 311 to rotate the inhalation passage 311 to be rotated according to an inhalation sucked through the inhalation passage 311, and a plurality of coils 331 to 334 installed at an inner side of the exhalation passage 311 to generate an induction current according to an alternate magnetic field caused by a rotation of the of the turbine 320.

The turbine 320 includes a plurality of blades 321 to 324 having magnetism, and the odd numbered blades 321 and 323 among the plurality of blades 321 to 324 and the even numbered of blades 322 and 324 among the plurality of blades 321 to 324 may have the mutually opposite magnetism. For example, when the turbine 320 has four blades 321 to 324 and the respective blades are referred to as first to fourth blades, the first and third blades may have an N pole while the second and fourth blades may have an S pole.

Regarding the plurality of coils 331 to 334, the odd numbered coils 331 and 333 and the even numbered coils 332 and 334 may have the mutually opposite magnetism. For example, when the signal generation unit 113 includes four coils 331 to 334 and the respective coils are referred to as first to fourth coils, the first and third coils are wound in the same direction, the second and fourth coils are wound in the same direction, and the first and third coils are wound in the different directions and the second and fourth coils are wound in the different directions.

The reason for setting the magnetism and the polarity of the turbine 320 and the plurality of coils 331 to 334 is to maximize the current induced through the plurality of coils 331 to 334 according to the rotation of the turbine 320.

Figure 6B:
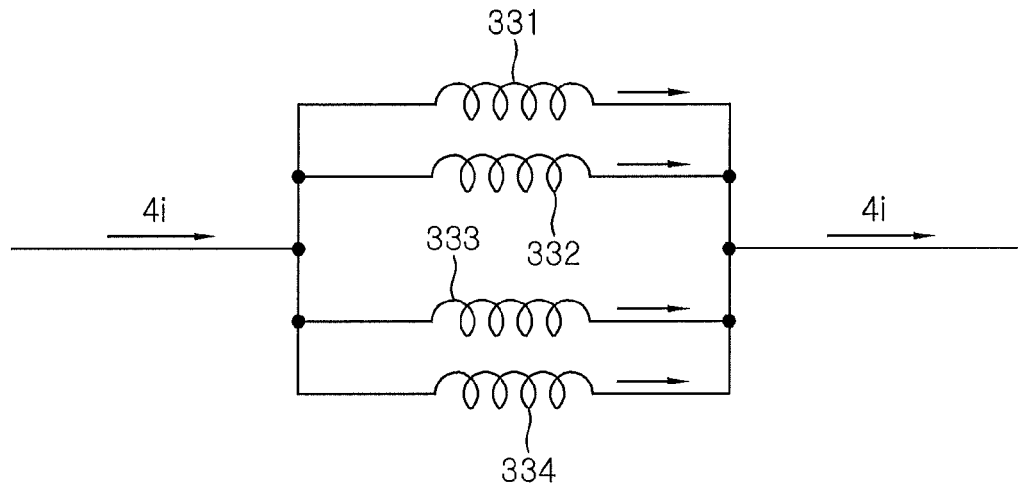

In addition, the plurality of coils 331 to 334 may be disposed to correspond to the positions of the plurality of blades 321 to 324 of the turbine 320 and may have the structure in which they are connected in parallel as illustrated in FIG. 6b, thereby further increasing the current induction effect over the change in a magnetic flux density.

An air tube 114 implemented to be made of silicon material and to have a cylindrical shape may be additionally attached to the signal generation unit 113 such that the air tube 114 can be inserted into the user's nose. Accordingly, inhalation into the user's nose and exhalation from the user's nose can pass only through the body 310 of the signal generation unit 113.

The respiration measurement sensor 110 may be driven as follows to derive information regarding the respiration rate.

First, whenever the user wearing the respiration measurement device inhales, the exhaust valve plate 314 is shut by a suction pressure according to the inhalation and the suction valve plate 313 is open to allow air to be introduced through the inhalation passage 311.

Then, the magnetized turbine 320 installed in the inhalation passage 311 rotates to cause a change in the magnetic flux density and the plurality of coils 331 to 334 installed on the inner side of the inhalation passage 311 detect the change in the magnetic flux density and generate an induction current.

Thus, the induction current generation period of the plurality of coils 331 to 334 is consistent with the inhalation generation period, and the value of the induction current generated through the plurality of coils 331 to 334 is proportional to the respiration rate (i.e., the inhalation amount) of the person wearing the respiration measurement device.

As a result, as shown in FIG. 5, the signal processing unit 130 can derive the respiration rate of the person wearing the respiration measurement device through the induction current generation period and the induction current value generated through the respiration measurement sensor 110.

Figure 7:
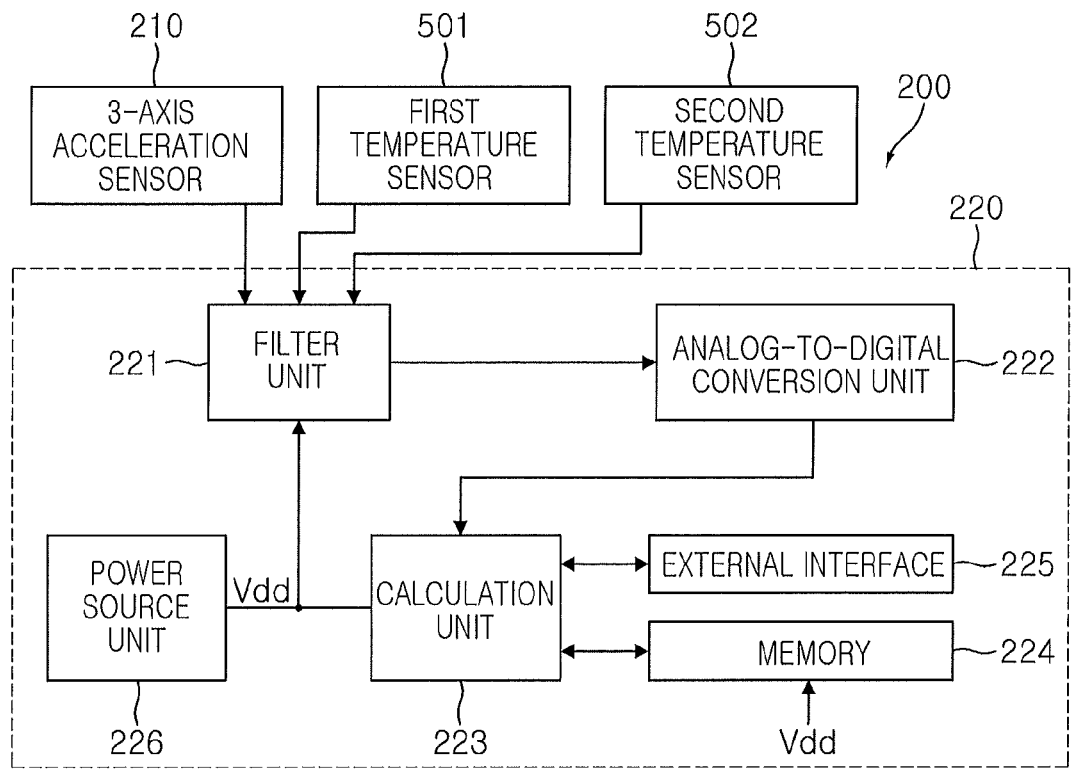
FIG. 7 is a schematic block diagram of an acceleration sensor according to an exemplary embodiment of the present invention.

FIG. 7 is a schematic block diagram of an acceleration sensor according to an exemplary embodiment of the present invention.

With reference to FIG. 7, a movement detection device 200 may include a 3-axis acceleration sensor 210 and a signal processing unit 220. The movement detection device 200 may further include one or more of temperature sensors 501 and 502 for measuring a skin temperature and/or an external body temperature as necessary. In this case, the movement detection device 200 may be one of the plurality of movement detection devices 201 to 203 of FIG. 1.

The 3-axis acceleration sensor 210 may be implemented in the form of a strain gage type sensor, a piezoelectric type sensor, a servo type sensor, and the like. The 3-axis acceleration sensor 210 detects an acceleration and vibration discriminately according to X, Y, and Z axes to three-dimensionally acquire the magnitude and direction of a movement of the user's body part on which the 3-axis acceleration sensor is positioned.

Figure 8:
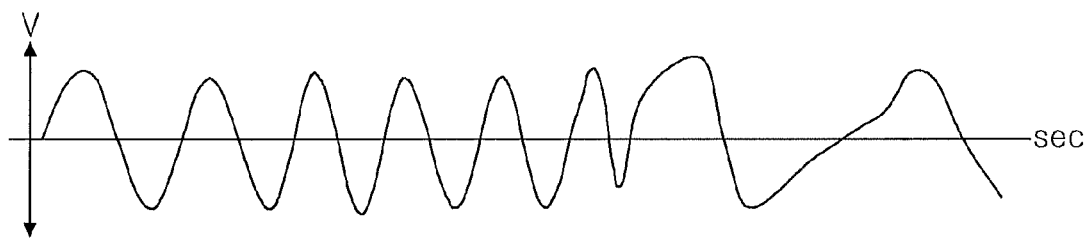
FIG. 8 illustrates an acceleration signal according to an exemplary embodiment of the present invention.

In this case, as shown in FIG. 8, the 3-axis acceleration sensor 210 may output an acceleration signal in the form of a DC+AC signal with respect to each axis according to the magnitude and direction of the movement of the user's body part where the 3-axis acceleration sensor 210 is positioned. Of course, the 3-axis acceleration sensor 210 may output an acceleration signal in the form of a DC signal or an AC signal with respect to each axis according to circumstances.

The signal processing unit 220 converts the magnitude and direction of the movement acquired by the 3-axis acceleration sensor 210 and a skin temperature and/or external body temperature into a signal form recognizable to the controller 300, and provides the converted signal to the controller 300.

Namely, the signal processing unit 220 includes a filter unit 221 converting signals inputted from the 3-axis acceleration sensor 210 and the first and second temperature sensors 501 and 502 into voltages and filtering and amplifying the same to improve signal characteristics, an analog-to-digital conversion unit 222 converting an output signal from the filter unit 221 into a digital signal, a calculation unit 223 analyzing a generation pattern of the digital signal from the analog-to-digital conversion unit 222 to calculate the amount of a user's movements and movement patterns, a memory 224 storing an output from the calculation unit 223, an external interface 225 providing an output from the calculation unit 223 or the information stored in the memory 224 to the controller 300, and a power source unit 226 providing power required for driving the signal processing unit 220.

In the above description, the movement detection device 200 includes the 3-axis acceleration sensor 210, but the present invention is not limited thereto and, of course, the 3-axis acceleration sensor 210 may be replaced by a gyro sensor, a G-sensor, and the like, within the coverage in which it can detect the direction and amount of the movement of each body part.

In addition, in an exemplary embodiment of the present invention, in order to increase the signal transmission efficiency and management efficiency of the respiration measurement device 100 and the plurality of movement detection devices 201 to 203, the respiration measurement device 100 and the plurality of movement detection devices 201 to 203 may be coupled by a single device, namely, by a docking station.

Figure 9:
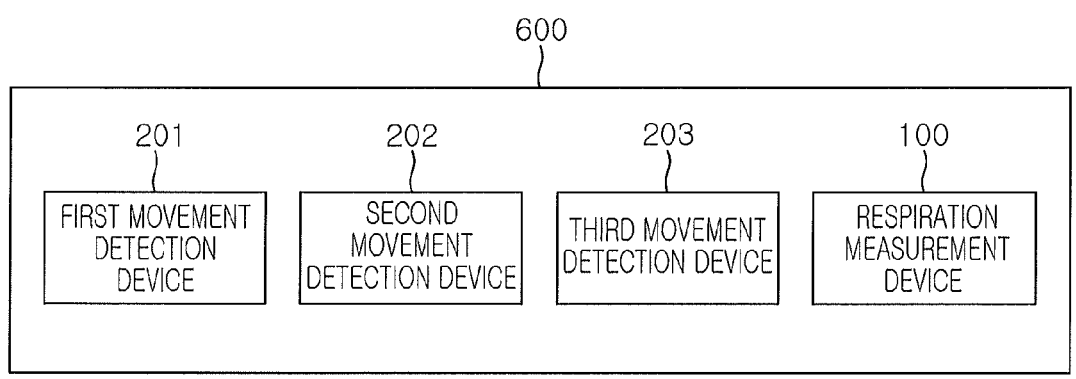
FIG. 9 is a schematic block diagram of a docking station according to an exemplary embodiment of the present invention.

FIG. 9 is a schematic block diagram of a docking station according to an exemplary embodiment of the present invention. With reference to FIG. 9, it is noted that the respiration measurement device 100 and the plurality of movement detection devices 201 to 203 are coupled by a single device Accordingly, in the present exemplary embodiment, signals from the respiration measurement device 100 and the plurality of movement detection devices 201 to 203 can be transmitted to the external electronic device 400 at a time through the docking station 600, or the respiration measurement device 100 and the plurality of movement detection devices 201 to 203 can be simultaneously charged.

Namely, in the present exemplary embodiment, the operations of the respiration measurement device 100 and the plurality of movement detection devices 201 to 203 can be collectively or comprehensively controlled through the docking station 600.

As set forth above, according to exemplary embodiments of the invention, user's movements can be accurately recognized through the 3-axis acceleration sensor placed at typical positions where user's three-dimensional movements can be measured, and because a device for measuring the user's respiration is additionally provided, the intensity of exercise can be estimated, and thus, consumed calories can be accurately calculated.

In addition, the user's consumed calories normal times, as well as the user's consumed calories in activity, can be measured, and because the user's respiration can be measured, the application fields of the present invention can be variably extended to, for example, monitoring of a person having a disease related to respiration.

While the present invention has been shown and described in connection with the exemplary embodiments, it will be apparent to those skilled in the art that modifications and variations can be made without departing from the spirit and scope of the invention as defined by the appended claims.

What is claimed is:

1. A portable device for measuring a consumed calorie, the device comprising:
    a respiration measurement device measuring an amount of air inhaled into a user's nose to acquire and output a respiration signal, and including a signal generation unit having a cylindrical body;
    a plurality of movement detection devices acquiring and outputting acceleration signals at least one of reflecting or indicating a magnitude and direction of a movement of corresponding parts of the user's body; and
    a controller recognizing an amount of a user's movements and movement patterns by analyzing the acceleration signals, recognizing an intensity of an exercise by analyzing the respiration signal, and calculating consumed calories in consideration of the amount of a user's movements, the movement patterns, and the intensity of the exercise;
    wherein the cylindrical body of the signal generation unit is coaxial with an air tube insertable at least partly into a user's nose.

2. The device of claim 1, further comprising one or more temperature sensors measuring one or more of a user's mouth temperature, a user's skin temperature, and an external body temperature.

3. The device of claim 2, wherein the controller calculates the consumed calories further in consideration of one or more of the user's mouth temperature, the user's skin temperature, and the external body temperature, in addition to the amount of movements, the movement patterns, and the respiration rate.

4. The device of claim 1, wherein the respiration measurement device comprises:
    a respiration measurement sensor measuring the amount of air inhaled into the user's nose; and
    a signal processing unit calculating the respiration rate from the amount of air which has been measured by the respiration measurement sensor, converting the respiration amount into a signal recognizable to the controller, and outputting the converted signal.

5. The device of claim 4, wherein the respiration measurement sensor comprises:
    a glasses frame having a nose cover formed to cover the user's nose; and
    wherein the signal generation unit is placed on the nose cover and generates a signal corresponding to the amount of air inhaled into the user's nose or exhaled from the user's nose.

6. The device of claim 5, wherein the cylindrical body comprises:
    an inhalation passage;
    a turbine installed in the inhalation passage so as to rotate according to inhalation through the inhalation passage; and
    a plurality of coils installed at an inner side of the inhalation passage in order to generate an AC signal according to alternate magnetic fields resulting from the rotation of the turbine.

7. The device of claim 6, wherein the cylindrical body further comprises:
    an exhalation passage accommodating the inhalation passage therein;
    a suction valve plate installed in the inhalation passage and opened only for inhalation;
    a discharge valve plate installed in the exhalation passage and opened only for exhalation; and
    a frame fixing the inhalation passage in the interior of the exhalation passage and supporting the position of the turbine.

8. The device of claim 5, wherein the respiration measurement sensor further comprises a mouth piece implemented to be separated from the glasses frame or placed on the glasses frame such that it is positioned at a lower side of the nose cover.

9. The device of claim 8, wherein the mouth piece comprises a temperature sensor for measuring the user's mouth temperature.

10. The device of claim 4, wherein the signal processing unit comprises:
    a filter unit converting an input signal into a voltage signal, filtering the converted voltage signal, and amplifying the filtered voltage signal;
    an analog-to-digital conversion unit converting an output from the filter unit into a digital signal;
    a calculation unit analyzing a generation pattern of the digital signal to calculate the amount of breath; and
    an external interface providing an interface with the controller.

11. The device of claim 10, wherein the signal processing unit comprises:
    a memory storing an output from the calculation unit; and
    a power source unit providing a power source required for driving the signal processing unit and charging the power source by using an AC signal provided from the respiration measurement sensor.

12. The device of claim 1, wherein each of the plurality of movement detection devices comprises:
    a 3-axis acceleration sensor acquiring the magnitude and direction of a movement of the corresponding body part; and
    a signal processing unit outputting the magnitude and direction of a movement acquired by the 3-axis acceleration sensor in the form of a signal recognizable to the controller.

13. The device of claim 12, wherein the signal processing unit comprises:
    a filter unit converting an input signal into a voltage signal, filtering the converted voltage signal, and amplifying the filtered voltage signal;
    an analog-to-digital conversion unit converting an output from the filter unit into a digital signal;
    a calculation unit analyzing a generation pattern of the digital signal to calculate the amount of breath; and
    an external interface providing an interface with the controller.

14. The device of claim 13, wherein the signal processing unit further comprises a memory storing an output from the calculation unit.

15. The device of claim 12, wherein each of the plurality of movement detection devices comprises one or more of a temperature sensor for measuring a skin temperature and an external body temperature.

16. The device of claim 12, wherein when the controller calculates consumed calories, it calculates adjustable consumed calories in consideration of signals acquired by the respiration measurement device and the plurality of movement detection devices.

17. The device of claim 1, wherein the respiration measurement device and the plurality of movement detection devices are coupled to a docking station.

* * * * *